(12) United States Patent
Lautenschlaeger et al.

(10) Patent No.: US 10,646,194 B2
(45) Date of Patent: May 12, 2020

(54) AUTOMATIC AIR-CALIBRATION

(71) Applicants: Siemens Healthcare GmbH, Erlangen (DE); DEDICATED2IMAGING, LLC, Portsmouth, NH (US)

(72) Inventors: Stefan Lautenschlaeger, Nuremberg (DE); Eric Bailey, North Hampton, NH (US); Charles Landry, Seabrook, NH (US)

(73) Assignees: Siemens Healthcare GmbH, Erlangen (DE); Dedicated2Imaging, LLC, Portsmith, NH (US)

( * ) Notice: Subject to any disclaimer, the term of this patent is extended or adjusted under 35 U.S.C. 154(b) by 243 days.

(21) Appl. No.: 15/911,218

(22) Filed: Mar. 5, 2018

(65) Prior Publication Data

US 2019/0269378 A1 Sep. 5, 2019

(51) Int. Cl.
*A61B 6/00* (2006.01)
*G01N 23/046* (2018.01)
*A61B 6/03* (2006.01)

(52) U.S. Cl.
CPC ............ *A61B 6/582* (2013.01); *A61B 6/4405* (2013.01); *G01N 23/046* (2013.01); *A61B 6/035* (2013.01); *G01N 2223/419* (2013.01); *G01N 2223/612* (2013.01)

(58) Field of Classification Search
None
See application file for complete search history.

(56) References Cited

U.S. PATENT DOCUMENTS 6,256,404 B1 7/2001 Gordon et al.
2019/0192106 A1* 6/2019 Rozas .................... A61B 6/032

FOREIGN PATENT DOCUMENTS

WO WO2017180566 A2 10/2017

\* cited by examiner

*Primary Examiner* — Hoon K Song

(57) ABSTRACT

A computed tomography system has an x-ray source, x-ray detector, a gantry, and a controller configured to automatically initiate an air-calibration using the source and detector with air in an air space and to determine gain values for channels of the detector from the automatically initiated air-calibration. A computed tomography system having a patient bore, a controller, an x-ray source, and a detector is calibrated by receiving a setting for a medical scan to be performed by the computed tomography system for a particular patient, the setting being one of a plurality of optional values, scanning air and not the patient in the patient bore with the source and the detector using the setting, determining a gain value based on the scanning with the setting and not the other optional values, and scanning the patient with the source and the detector using the setting and the gain value.

18 Claims, 4 Drawing Sheets

AUTOMATIC AIR-CALIBRATION

BACKGROUND

The present embodiments relate to calibration of computed tomography (CT) systems. For consistent high image quality, CT scanners perform an "air-calibration" scan typically once a day. For the air-calibration, no objects are in the beam during the scan. Certain electrical and optical components in the CT detector system (e.g. photodiodes, scintillators, op amps, etc.) are sensitive to "gain drift," or have gain and offset values that are only suitable for a range of operating conditions. The CT system has a different gain calibration number for each detector channel (of which there can be thousands of channels). Without recalibration over time or change in environment, the gains may be incorrect, and this "gain drift" may result in unpleasant or unacceptable artifacts in the CT image. For example, a "ring", "partial ring", or "dagger" artifact results for sub-optimal gain calibration.

To prevent artifacts, an air-calibration is recommended to be performed at least once a day, once per shift, and/or whenever large environmental changes (e.g. in temperature) are experienced. The air-calibration consumes time and is done for all x-ray voltages, focal spot sizes, and x-ray filters. Calibration is also important in the case of mobile CT scanners, which operate in different environmental conditions due to their mobile nature.

For consistent image quality in a mobile CT scanner, air-calibration prior to every patient or at every differing location may be advised. Although no object/phantom needs to be placed in the CT scanner, air-calibration is initiated manually. As a result, air-calibration may not occur when appropriate. The recommended times may not be used and/or may not be appropriate for a given situation. Additionally, especially for mobile CT scanners, for which there is no control room or exam room, air-calibrations potentially result in scatter radiation exposure outside the scanner.

SUMMARY

By way of introduction, the preferred embodiments described below include methods and systems for performing an air-calibration of a CT system. A CT system automatically initiates an air-calibration. Gain values for channels of an x-ray detector are determined by a controller from the automatically initiated air-calibration. The automatic initiation of the air-calibration may be triggered by the presence of a patient in the air space, in response to activation to start a scanning of the patient, and/or in response to sensing a change that may affect gain (e.g. temperature or humidity).

In a first aspect, a CT system is provided. The system includes an x-ray source and an x-ray detector. A gantry is configured to move the x-ray source and x-ray detector relative to an air space. A controller is configured to automatically initiate an air-calibration using the x-ray source and x-ray detector with air in the air space and to determine gain values for channels of the x-ray detector from the automatically initiated air-calibration.

In a second aspect, a method is provided for calibrating a CT system having a patient bore, a controller, an x-ray source, and a detector. A controller receives a setting for a medical scan to be performed by the CT system for a particular patient. The setting is one of a plurality of optional values. The x-ray source and the detector scan air and not the patient in the patient bore. The controller determines a gain value based on the scanning with the setting and not the other optional values. The x-ray source and the detector scan the patient using the setting and the gain value.

In a third aspect, a method is provided for calibrating a vehicle-dispatched mobile CT system having an x-ray source, an x-ray detector, a gantry, and a controller. The gantry moves the x-ray source and the x-ray detector relative to an air space. The controller automatically initiates an air-calibration using the x-ray source and x-ray detector with air in the air space. The controller determines gain values for channels of the x-ray detector from the automatically initiated air-calibration.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Conditions or usage of a CT scanner triggers air-calibration. By using a sensor, the mobile CT scanner may automatically detect whether a new air-calibration is indicated (e.g. if temperature, humidity, or other contextual parameters have changed since the last air-calibration). If this is the case, the air-calibration is initiated automatically. The air-calibration may be automatically initiated if the scanner is started up newly (i.e., powered on). Automatic initiation may occur for each patient, such as automatically initiating air-calibration once a patient is to be scanned. This arrangement benefits from performing air-calibration specific to the settings for scanning the patient. If one or more of the above-mentioned preconditions are fulfilled, the air-calibration is executed automatically, and the corresponding measures are used for subsequent scanning and imaging.

In some cases, a load sensor of a head or patient holder provides information that there is no load on the head holder. The automatic initiation of air-calibration is performed as long as there is no patient in the CT scanner. Alternatively, the air-calibration may be executed with the patient present in the CT system or with a load on the head holder, such as where a gantry may move the source and detector to a separate part of the bore for air-calibration. This allows air-calibration to be shortened for the x-ray source voltage, x-ray tube focus spot, and x-ray filter particular for the patient to be scanned.

Automatic initiation of air-calibration offers the advantages of improved image quality. Rather than irregularly following a recommended schedule, the air-calibration is performed automatically as needed. The risk of image artifacts interfering with diagnosis is reduced due to removing the manual aspect and due to triggering when appropriate rather than based on an arbitrary manufacturer recommended schedule. Optimized workflows are provided because the air-calibration is performed automatically.

Figure 1:
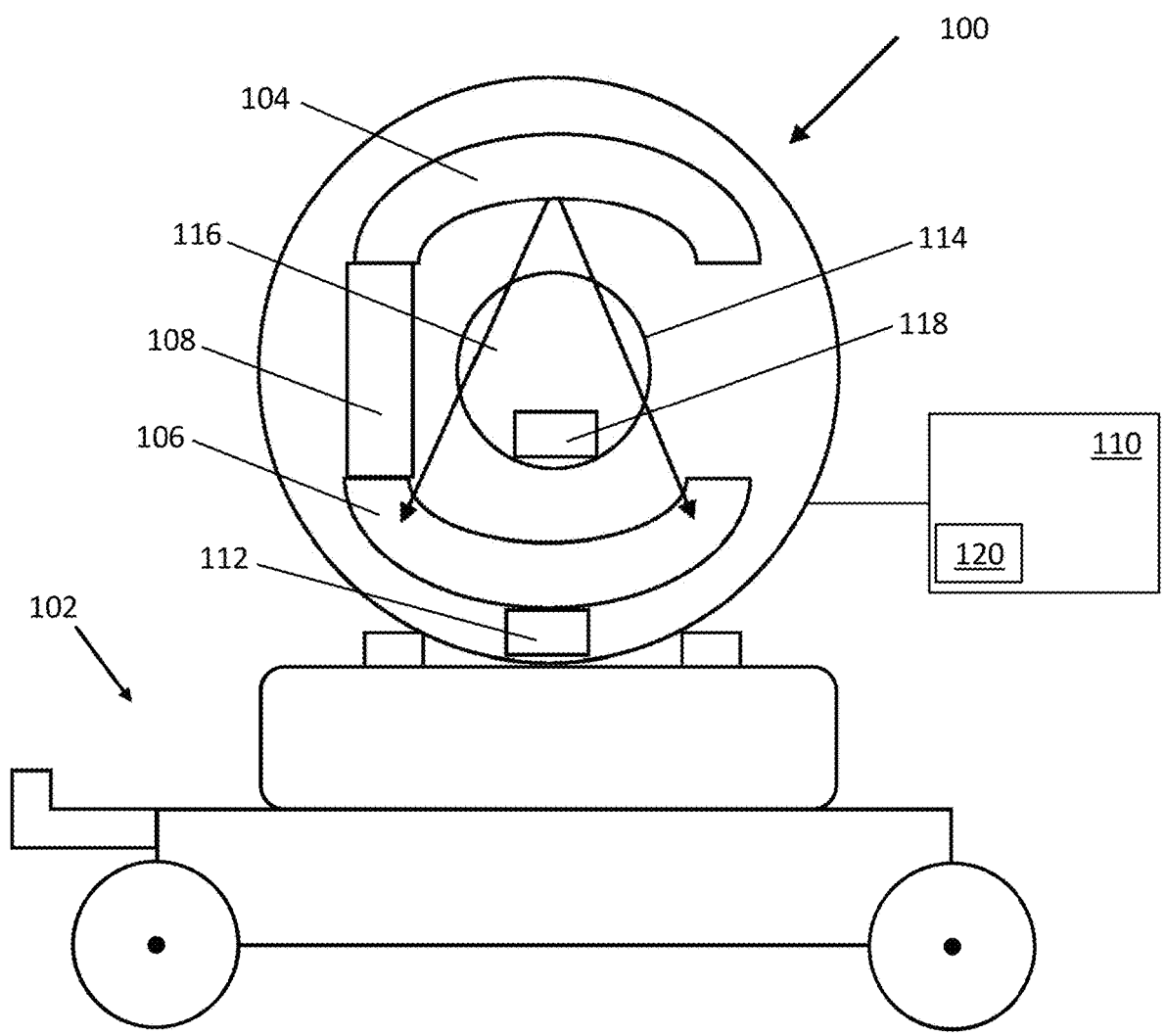
FIG. 1 is a schematic diagram of an example mobile CT system.

FIG. 1 is a schematic diagram of an example mobile CT system 100. The CT system 100 is configured to perform an air-calibration automatically, reducing the risk of imaging artifacts. The method of FIG. 4 or another method is implemented by the system 100. A sensor and/or patient scan activation is used to automatically initiate air-calibration.

Figure 3:
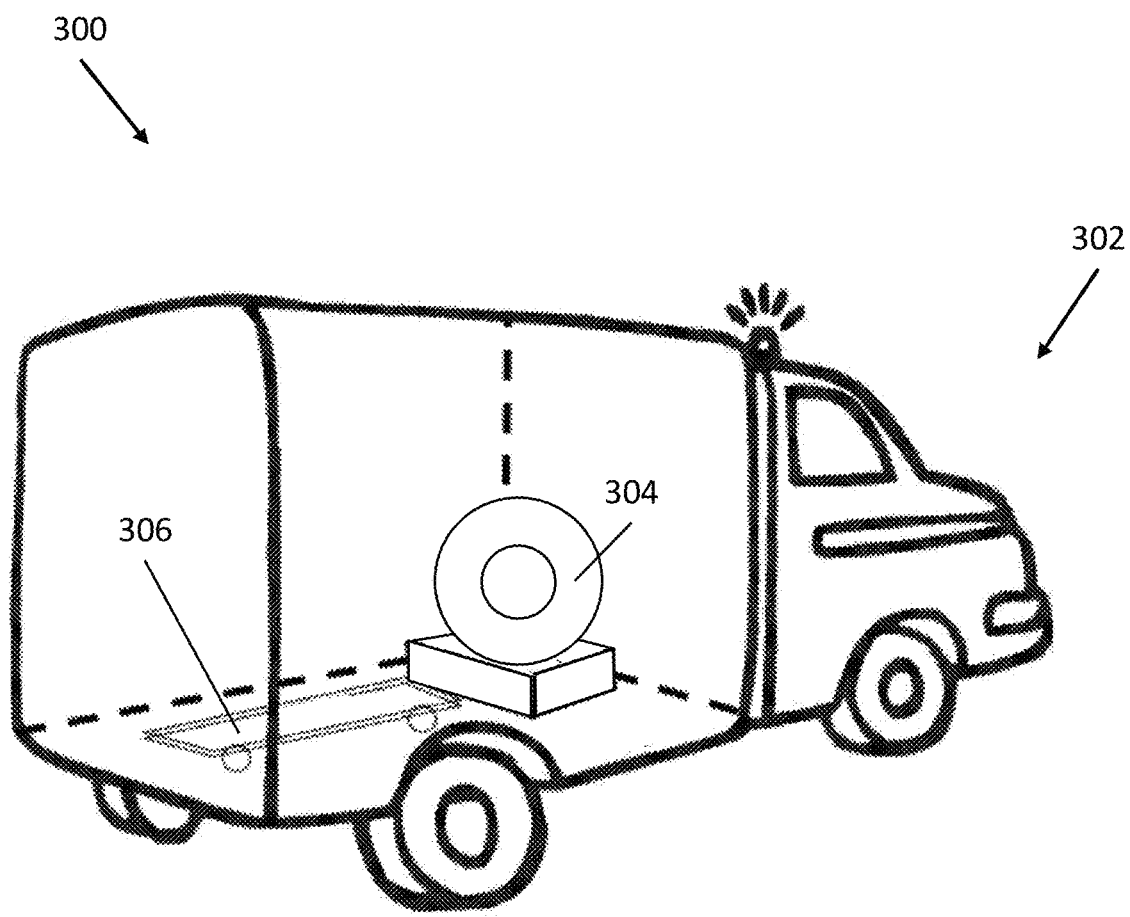
FIG. 3 is a schematic diagram of one example of a vehicle-dispatched mobile CT system.

The CT system 100 may be a mobile CT system capable of moving to different locations to perform CT scans of patients. For example, the CT system 100 may be installed on a cart 102 with wheels. The cart 102 may be configured to move under its own power and/or to be moved by an external force provided by, for example, an operator. Additionally or alternatively, the CT system 100 may be configured to be deployed via a vehicle. In some cases, the system 100 is installed in an ambulance, for example, as shown in FIG. 3. The system 100 may be configured to scan patients within the ambulance. Additionally or alternatively, the system 100 may be dispatched via the ambulance and be moved within or outside of the ambulance for scanning. In one embodiment, the CT system disclosed in WO 2017/180566, published Oct. 19, 2017, is used.

Additionally or alternatively, the CT system 100 may be stationary. For example, the system 100 may be installed in an imaging room without wheels and/or fixed in place. In such cases, a patient may be brought to the CT system 100 for scanning, instead of moving the CT system 100 to the patient.

The CT system 100 includes an x-ray source 104, an x-ray detector 106, a gantry 108 supporting the source 104 and detector 106, a controller 110, and a sensor 112. The gantry 108 and corresponding housing provides a patient bore 114 that defines an air space 116 in which part of the patient is to be placed for scanning. The patient bore 114 contains a load sensor 118. The controller 110 is configured to move the gantry 108, activate the source 104, and read measurements from the detector 106 for air-calibration. The controller 110 determines a gain for each channel of the detector 106 and applies the gains during CT imaging of a patient.

Additional, different, or fewer components may be provided. For example, the sensor 112 is not provided where initiation is based on activating the CT system to scan a patient currently positioned in the bore 114. As another example, a Positron Emission Tomography (PET) detector is provided for concurrent imaging with the x-ray source 104 and detector 106. As a further example, a Single Photon Emission Computed Tomography (SPECT) detector is provided for concurrent imaging with the x-ray source 104 and detector 106. In yet another example, the load sensor 118 is not provided.

The x-ray source 104 may be configured to emit x-rays into the air space 116. The source 104 is mounted on the gantry 108, across from the detector 106. The source 104 is rotated around the air space 116 to emit x-rays into the air space 116 from different angles. During air-calibration, the x-ray source 104 may be moved from the air space 116 to another part of the bore 114. The x-ray source 104 emits x-rays into the bore 114 based on different voltages and x-ray source focus spots. The x-ray source 104 may have a single or multiple focal spots.

The x-ray detector 106 is configured to detect x-rays emitted by the source 104 across the air space 116. The x-ray detector 106 is a flat or curved substrate with sensors, such as a flat panel detector. Each sensor and electronics for each sensor form channels for detecting the x-rays incident on the sensor. The x-ray detector 106 may include any number of channels, such as hundreds or thousands. The x-ray detector 106 may be positioned opposite the x-ray source 104 on the gantry 108. The detector 106 acquires x-ray projections from different axial and longitudinal positions relative to the air space 116 which may be used to create a two- or three-dimensional image of the air space 116.

An X-ray filter may be included. More than one X-ray filter may be provided. Different filters are available for different imaging or scanning. The air-calibration may be performed separately for the different filters as different filters may result in different gains.

During air-calibration, the x-ray detector 106 may be moved from a patient-receiving portion of the air space 116 to another part of the bore 114. X-rays emitted into the bore 114 are detected on the channels of the detector 106. The gain for each of the channels of the detector 106 may be determined based on a measured response of each channel to the x-rays emitted by the source 104. The voltage, focus spot, and x-ray filter affect the gain. In some cases, an offset value for each channel is determined prior to the x-ray source 104 emitting any x-rays toward the detector 106.

The x-ray source 104 and x-ray detector 106 may be disposed on opposites sides of the air space 116. The gantry 108 rotates the source 104 and the detector 106 about the air space 116.

The gantry 108 supports the x-ray source 104 and x-ray detector 106 on opposite sides of the air space 116. The gantry 108 is a C-arm, tube, armature, or other frame for supporting and moving the x-ray source 104 and the detector 106 linearly, helically, or other movement pattern about the air space 116. The gantry 108 may move the source 104 and detector 106 around the air space 116 to emit and detect x-rays from multiple angles. Additionally, the gantry 108 may translate the source 104 and detector 106 along the length of the bore 114 so that the source 104 and detector 106 may image the air space from multiple angles and positions relative to the air space 116. During air-calibration, the gantry 108 may move the source 104 and the detector 106 from the patient-receiving portion of the air space 116 toward another portion of the bore 114 in which the patient is not positioned. For example, the gantry 108 may move the source 104 and detector 106 toward an air-calibration portion of the bore 114 and air space 116. After the calibration, the gantry 108 may move the source 104 and the detector 106 toward the patient-receiving portion of the air space 116 for imaging the patient. In some cases, for example when the patient is not present in the patient receiving portion of the air space 116, or where the air space 116 does not have a patient-receiving portion and an air-calibration portion, air-calibration may be performed in the air space 116 without the gantry moving the source 104 and detector 106 away from the patient-receiving portion of the air space 116.

The bore 114 defines the air space 116. The bore 114 is formed by a housing, framework, or other structure of the CT system 100. The bore 114 is a region in which the patient is placed for scanning. The bore 114 may have another portion separate from the patient-receiving portion of the air space 116 suitable for performing air-calibration. The air-calibration portion may be disposed along a longitude of the bore 114, adjacent to the patient-receiving portion of the air space 116. In some cases, a divider or shielding may separate the air-calibration portion of the bore 114 from the patient-receiving portion of the air space 116. For example, when the patient is present in the patient-receiving portion of the air space 116, air-calibration may be performed in the air-calibration portion of the bore 114 while a shield or divider separates the air-calibration portion from the patient-receiving portion of the air space 116 to reduce scatter radiation. Additionally or alternatively, air-calibration may be performed at a longitudinal distance from the patient-receiving portion of the air space 116 such that transmission of scatter radiation into the air space 116 is reduced without a shield or divider. In other embodiments, the air-calibration is performed in the portion of the bore 114 in which the patient is to be but not yet placed.

A load sensor 118 may be located in the air space 116 to detect the presence of a patient. The load sensor 118 may be a transducer, a hydraulic cell, a pneumatic cell, or a strain gauge. Additionally or alternatively, the load sensor 118 may be a switch or another kind of sensor. For example, the load sensor 118 may be a Hall effect sensor. The load sensor 118 may be located on top of, below, or integrated with a patient support of the air space 116. In some cases, the load sensor 118 is integrated in a head holder in the patient-receiving portion of the air space 116.

When a patient is present in the patient-receiving portion of the air space 116, the load sensor 118 detects the force from the patient when positioned in the bore 114 and communicates the presence to the controller 110. In some cases, when the load sensor 118 senses a load, the controller 110 may send a signal to lock a wheel of the cart 102 or otherwise prevent movement of the CT system 100.

The sensor 112 is a clock, thermometer, humidity, global position, or other sensor for measuring time, temperature, humidity, or geographical location. The sensor 112 is in communication with the controller 110. For example, the sensor 112 may measure time, temperature, humidity, or location with respect to the CT system 100 or ambient conditions. Additionally or alternatively, the sensor 112 may be integrated with the controller 110. Other sensors may be provided for measuring the environment, usage, and/or other characteristics related to the CT system 100.

The controller 110 is a processor, application specific integrated circuit, field programmable gate array, digital signal processor, or other device for controlling operation of the CT system 100. The controller 110 may include a memory 120 and an I/O interface. The controller 110 is in communication with the cart 102, source 104, detector 106, gantry 108, sensor 112, and load sensor 118. For example, the controller 110 may communicate with components of the CT system 100 via a bus, network and/or other interface. The controller 110 may be integrated or remote from the CT system 110. In some cases, the controller is located within the cart 102 or a housing of the CT system 100. The controller 110 is configured by firmware, software, and/or hardware.

The memory 120 or other memory is alternatively or additionally a non-transitory computer readable storage medium storing data representing instructions executable by a processor of the controller 110 or a processor implementing the automatic air-calibration. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

The controller 110 is configured to automatically initiate an air-calibration using the x-ray source 104 and x-ray detector 106 with air in the air space 116. The air-calibration uses part of the air space 116 not currently occupied by a patient. Initiating air-calibration may include the controller 110 causing the gantry 108 to move the source 104 and detector 106 to scan the air space 116, causing the source 104 to emit x-rays at the detector 106.

The controller 110 may initiate the air-calibration based on activation of the CT system 100 for scanning the patient. The controller 110 may perform the air-calibration using the same settings as for scanning the patient. The settings may include a voltage, a focus spot, or an x-ray filter.

For example, the patient may be inserted into the air space 116 and an operator selects one or more scan settings (e.g. voltage, focus spot, and/or x-ray filter) out of many possible scan settings to image the patient. When the operator activates the CT system 100 to scan the patient using the scan settings, the controller 110 initiates an air-calibration using the same voltage, focus spot, and/or x-ray filter by moving the source 104 and detector 106 toward the air-calibration portion of the bore 114. When the air-calibration is finished, the CT system 100 may indicate to the operator that the system 100 is ready to scan the patient (e.g. by illuminating a button) and the operator may provide input to start the patient scan (e.g. by pressing the button). Once pressed, the controller 110 causes the gantry 108 to move the source 104 and detector 106 toward the patient-receiving portion of the bore 114 and scans the patient. In another example, where the bore 114 does not have an air-calibration portion, the operator inputs a scan setting for a patient scan that is received by the controller 110. Before the patient is inserted into the bore 114, the controller 110 automatically performs an air-calibration with the source 104 and detector 106 using the input scan setting and generates gain values for the detector 106 that are valid for the scan setting. After air-calibration, the controller 110 indicates to the operator that the CT system 100 is ready for imaging. The operator inserts the patient into the bore 114 and the operator starts the scan. The CT system 100 scans the patient using the gain values and the input scan setting. In another example, the controller 110 receives a scan setting for imaging the patient, performs an air-calibration for the setting, and images the patient using the scan setting and gain values from the air-calibration without further input from the operator.

In a still further example, the last air-calibration was performed with a particular voltage, focus spot, and x-ray filter, and the controller 110 automatically initiates air-calibration if the controller 110 receives scan settings specifying a voltage, focus spot, or x-ray filter that is different than the last air-calibration.

The controller 110 may detect the presence of a patient in the air space 116 and initiate an air-calibration. For example, the load sensor 118 senses the presence of a patient in the air space 116 and sends a signal to the controller 110. In response to the signal, the controller 110 may initiate the air-calibration. Additionally or alternatively, the controller 110 initiates the air-calibration in response to activation of the CT system 100 for scanning and the presence of a patient in the air space 116. Alternatively, the controller 110 may initiate air-calibration in response to activation of the system for scanning the patient and the absence of any patient or object in the air space 116. For example, the absence of any patient or object in the air space 116 may be indicated by lack of a load on the load sensor 118.

Additionally or alternatively, the controller 110 may be configured to receive a contextual measure and automatically initiate the air-calibration when the contextual measure exceeds a threshold. If the contextual measure is within the threshold, the controller 110 may not automatically initiate air-calibration but may initiate air-calibration in response to user input manually specifying air-calibration. For example, the controller 110 may receive the contextual measure from the sensor 112. The contextual measure may be a measure of time, temperature, humidity, or location. For example, the controller 110 may automatically initiate an air-calibration if a threshold amount of time has elapsed, if there is a change in temperature or humidity exceeding a threshold, or if the CT system has moved a minimum distance since the last air-calibration. After verifying no patient is in the air space 116 and providing a warning, the air calibration is performed in response to a change in the conditions for the CT system 100. In some cases, the controller 110 automatically initiates an air-calibration if the CT system 100 is started for the first time (e.g., restart from cold) or if the last air-calibration occurred more than 8 hours ago. In one example, the threshold may be based on the settings and context of the last air-calibration. For example, if last air-calibration was performed at 68° Fahrenheit, the controller 110 may automatically initiate air-calibration when the controller 110 receives a contextual measure indicating a temperature of less than 58° F. or more than 78° F.

The controller 110 determines the gain values for the channels of the x-ray detector 106 based on the automatically initiated air-calibration. For example, the controller 110 may determine gain values for the detector 106 that are valid for the voltage, focus spot, and x-ray filter settings during air-calibration and patient scanning. Where the air-calibration used a subset of the possible voltage, focus spot, and x-ray filter settings, the controller 110 determines gain settings for the channels of the detector 106 that are valid for the same subset of voltage, focus spot, and x-ray filter settings during scanning.

Figure 2:
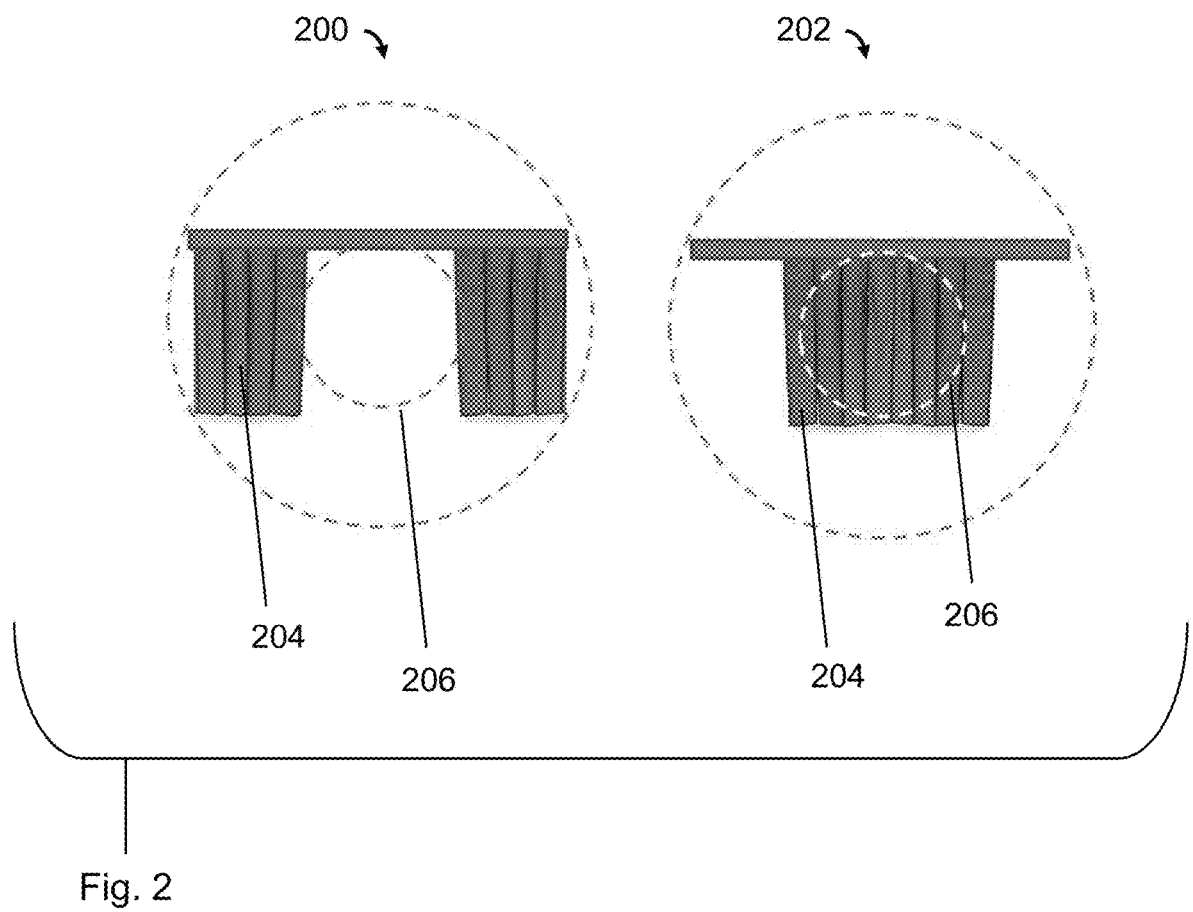
FIG. 2 is a schematic diagram of one embodiment of radiation-blocking curtains for a CT system.

FIG. 2 is a schematic diagram of one embodiment of radiation-blocking curtains for a CT system. The curtains 204 may be made out of an x-ray blocking material, such as lead. In an open position 200, the curtains 204 reveal the bore 206 of the CT system. The radiation blocking curtains 204 may be a pair of curtains that meet together in front of the bore 206. Additionally or alternatively, there may be only one curtain 204 provided in front of the bore 206. For example, the radiation blocking curtain 204 may be formed as a shade that extends from the top to the bottom of the bore 206.

In a closed position 202, the curtains conceal the bore 206. The curtains may be used with the CT system 100 shown in FIG. 1. For example, the curtains 204 may be mounted on the outside of the CT system 100 or within the bore 114 such that the curtains 204 cover the part of the bore 114 into which x-rays are pass for air calibration. While in the closed position 202, the space outside the bore 114 is blocked form the space in the bore 114 used for air calibration. The curtains 204 may separate a patient region within the bore 114 from an air-calibration region within the bore 114, such as for reducing exposure of the patient to x-rays from air calibration while the patient is positioned in the bore 114 for patient scanning.

The controller of the CT system may cause the curtains 204 to slide between the open 200 and close 202 positions. The curtains 204 may be opened 200 to allow for a patient or object to be loaded into or removed from the bore 206 of the CT system. Additionally or alternatively, when a load is removed from the load sensor in the bore, the controller 110 may cause the curtains 204 to automatically open.

When the CT system is scanning or performing an air-calibration, the controller may automatically cause the curtains 204 to be moved to the closed position 202. While closed, the curtains 204 reduce the amount of scatter radiation from the x-ray source that exits the CT system and/or is applied to the patient. In some cases, the curtains 204 are flexible so that when a head of the patient is present in the bore 206 during scanning or air-calibration, the curtains 204 bend and form around a neck or body of the patient in the closed position 202.

FIG. 3 is a schematic diagram of one example of a vehicle-dispatched mobile CT system 300. The mobile system 300 is configured to image patients in the field or away from medical facilities.

The mobile system 300 includes a vehicle 302, a CT system 304, and a patient support 306. In one embodiment, the CT system 304 is the CT system 100 as described in FIG. 1.

The vehicle 302 may deploy the CT system 304 away from a hospital and bring the system 304 to the locations of the patients, such as being in an ambulance. The CT system 304 may be configured to scan patients within the vehicle 302. Additionally or alternatively, the system 100 may be dispatched in the vehicle 302 and be moved within or outside of the vehicle 302 for scanning.

For example, paramedics or first responders may bring an ambulance 302 with a CT system 304 on calls where a stroke, head trauma, or other injury indicating a CT scan is present. Prompt imaging with the mobile CT system 304 allows earlier diagnosis of injuries and assessment of the appropriate level of care, whether a general hospital or a specialized brain trauma center. The patient may then be delivered to the appropriate medical facility, decreasing the time before care appropriate for the injury shown by the CT scan. For strokes, the time to treatment may have a large effect on quality of life and function for a patient.

The CT system 304 is configured to automatically perform an air-calibration. Because conditions in the field may change more dramatically and more rapidly than in a hospital, for example, the CT system 304 may be configured to detect a change in a context measure such as time, temperature, humidity, or location and automatically perform an air-calibration to calculate gain values for an x-ray detector of the CT system 304. Additionally or alternatively, the CT system 304 is configured to perform an air-calibration for each patient. After configuring the CT system 304 for the patient (e.g., setting a voltage, focus spot, and x-ray filter), the air-calibration is performed before scanning the patient. The air calibration is performed for only the subset of the available voltages, focus spots, and x-ray filters of the CT system 304 to be used for that patient. By performing an air-calibration on less than the full range of available voltages, focus spots, and x-ray filters, the CT system 304 may perform a quicker calibration prior to imaging to decrease the length of the imaging process while reducing the likelihood of imaging artifacts due to changing conditions since the last air-calibration.

The patient support 306 may be maneuvered to support the body of the patient when the head of the patient is in the mobile CT system 304. The patient support 306 may abut or dock with the CT system 304.

Figure 4:
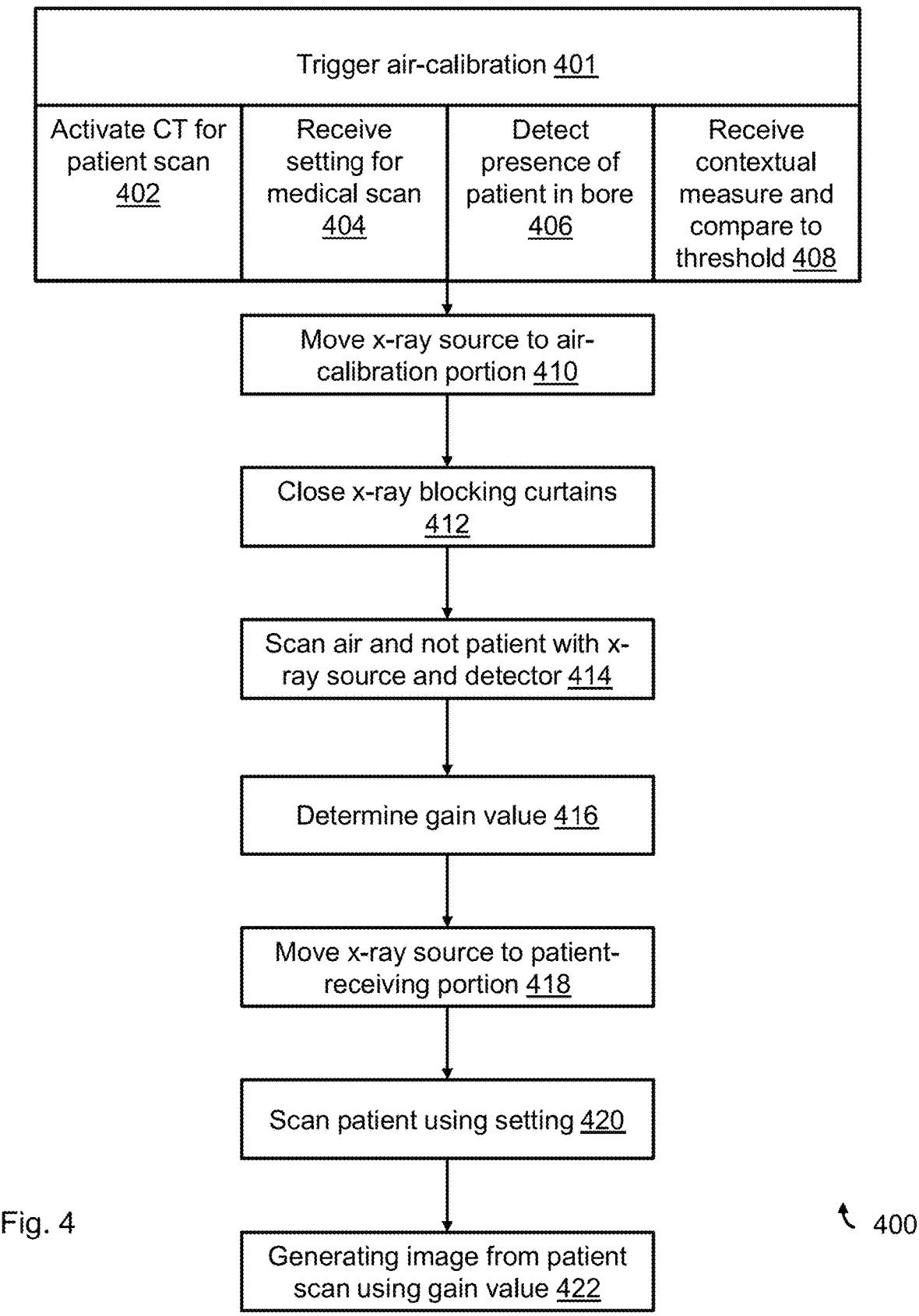
FIG. 4 is a flow chart diagram of one embodiment of a method for calibrating a CT system.

FIG. 4 is a flow chart diagram of one embodiment of a method 400 for air-calibrating a CT system having a patient bore, a controller, an x-ray source, and a detector. In one example, the CT system is a mobile or vehicle-dispatched CT system, which is more likely to be subjected to a change in conditions, that performs the method 400. One or more events may trigger the CT system 100 to perform an air-calibration. The gain values determined from the air-calibration may be used in a patient scan by the CT system 100.

The CT system 100 depicted in FIG. 1, the CT system 304 of FIG. 3, or another CT system may perform the calibration method 400. For example, acts 414 and 420 are performed by the source and detector of the CT system. Acts 410 and 418 are performed by the gantry. Acts 404, 408, and 416 are performed by the controller of the CT system and may use one or more sensors or user interfaces. Act 406 is performed by a load sensor with the controller.

The acts of the method are performed when the CT system is activated for scanning a patient or when another change in conditions (e.g. time, temperature, humidity, or location) has occurred. The method may be performed at other times, for example, at startup of the CT system.

The acts are performed in the order shown (e.g. top to bottom or numerical) or other orders. For example, acts 412 and 410 may be performed in any order or simultaneously. As another example, acts 404, 406, and 408 may be performed in any order or simultaneously.

Additional, different, or fewer acts may be provided. For example, the method is performed without one, two, or all of acts 402, 404, 406, and 408. In another example, act 410, 412, and/or 418 is not performed.

In another example, a sub-set of the acts are used for a vehicle-dispatched mobile CT system with a bore having a patient-receiving portion and a separate air-calibration portion. The source and detector are moved with a gantry according to acts 410 and 418, automatically initiate air calibration according to acts 404, 406, and/or 408, scan air in act 414, determine gain values according to act 416, and to scan the patient according to act 420. In a further example, a different sub-set of the acts are used for a vehicle-dispatched mobile CT system with a bore using the same air space for air calibration and patient scanning. The air calibration is initiated according to acts 404 and/or 408. Act 410 is not performed. The air is scanned in act 414. Gain values are determined according to act 414, and the patient is scanned according to act 420.

In act 401, the CT system triggers air-calibration. A controller receives indication of the occurrence of the trigger event and causes the CT system to perform air calibration. Automatically triggered air calibration results in up-to-date gains or gains appropriate for a given situation rather than relying on gains that may be out of date or not appropriate for a given situation. Using a trigger for air calibration may avoid reliance on generalized recommendations or failure to follow the recommendations.

Any trigger event may be used. Acts 402, 404, 406, and 408 indicate four examples. Other acts or combinations of acts may be used as triggers for the air calibration.

In act 402, the CT system is activated for scanning the patient. The CT system is activated for scanning based on operator input. The CT system may activate air-calibration based on just the activation for a patient scan. The patient is positioned in the bore, the scan settings for scanning the patient are entered, and any safety checks are performed. Then, the user activates the CT system for scanning the patient, such as depressing a scan button. Rather than immediately scanning the patient in response, the air calibration is performed first in response to the activation.

In act 404, a setting for a medical scan to be performed by the CT system for a particular patient is received by the controller. For example, the CT system may be activated for scanning and initiate air-calibration when the CT system receives a setting for a medical scan of the patient. The setting is one of a plurality of optional values for medical scan settings. For example, the setting may specify a voltage, a focus spot, and/or a x-ray filter. The x-ray source may be operable at different voltages, focus spots, and x-ray filters and the setting may specify a particular voltage, focus spot, and/or x-ray filter. The setting may be input by an operator or determined automatically, for example, based on other scan settings.

Based on the received scan setting, the controller may initiate air-calibration of the CT system. For example, the controller may compare the received scan setting to a previous scan setting for which an air-calibration was performed. If the settings are different, the controller may initiate air-calibration. In some cases, where the received setting is similar or identical to the previous scan setting, the controller may not initiate air-calibration and may initiate scanning of the patient.

In act 406, the controller detects the presence of the patient in the bore and automatically initiates air-calibration. In another example, the CT system is activated for scanning and initiates air-calibration when the CT system detects the presence of the patient in the bore. In some cases, the controller allows air-calibration of the CT system when the controller detects the absence of the patient in the bore and another trigger, but not when the controller detects the presence of the patient in the bore.

The presence or absence of the patient in the bore may be indicated by a load sensor in the bore. For example, the load sensor may be integrated in a head rest in a patient-receiving portion of the bore. The load sensor may communicate with the controller a signal indicating the presence or absence of a load or patient in the bore. In some cases, the presence or absence of the patient is indicated based on input from the operator.

In act 408, the controller receives a contextual measure, compares the contextual measure to a threshold, and initiates air-calibration based on the outcome of the comparison. For example, the controller may automatically initiate air-calibration when the contextual measure is above or below a threshold, or within or without a range of values.

The contextual measure may be a measure of time, temperature, humidity, or location. In some cases, the temperature or humidity may be sensed internal to the CT system. In other cases, the temperature and humidity are measures of ambient temperature and humidity. A sensor of the CT system may sense the temperature and humidity. For example, the sensor may be integrated in the bore, on the gantry, or with the controller. In some cases, the temperature and humidity are indicated by an external source, for example over a network connection from an internet resource.

When the contextual measure is a measure of time, the contextual measure of time may indicate the amount of time elapsed since the last air-calibration was performed by the CT system. Additionally or alternatively, the contextual measure may indicate the length of time since startup of the CT system, or the number of work shifts (e.g. 8 to 12-hour periods) that have passed since the last air-calibration. For example, the controller may automatically initiate air-calibration when the last air calibration was more than 24 hours ago, when the CT system was started in the last hour and an air-calibration has not been performed, or when more than one work shift has passed since the last air-calibration.

When the contextual measure is a measure of temperature or humidity, the contextual measure may be sensed by a sensor on the CT system, a sensor integrated with the controller, or communicated by an external source to the controller, for example, a weather service on the Internet. The contextual measure of temperature or humidity may indicate the ambient temperature or humidity, the temperature or humidity of the bore, or the temperature or humidity of scanning components such as the source or detector.

When the contextual measure is a measure of location, a sensor may indicate to the controller the current position or a distance traveled. For example, the sensor may be a global positioning system receiver that outputs geolocation and/or time information to the controller. The controller may compare the current position to previous positions and automatically initiate air-calibration if the distance between the positions is above a threshold. An acceleration sensor may indicate a change in location, and the controller initiates in response to the change.

The controller may automatically initiate air calibration based on one or more of the conditions described with respect to acts 401, 402, 404, 406, and 408. In one example, the controller receives a setting for a medical scan, compares the setting to a previously received setting for which an air calibration was performed, receives a contextual measure, compares the contextual measure to a threshold, and automatically initiates air-calibration if the received scan setting is different from the previous scan setting and/or if the contextual measure is beyond the threshold. In another example, when the CT system is activated for scanning a patient, the controller receives scan settings, detects the presence of the patient in the bore, receives a contextual measure, and initiates air-calibration. In a further example, once the CT system is activated for a patient scan, the controller initiates air-calibration when the presence of the patient in the bore is detected and based on a comparison of a received contextual measure to a threshold. In a still further example, the controller initiates air-calibration when the CT system is activated for a patient scan, the controller has received a setting for a medical scan, the presence of a patient in the bore is detected, and based on the comparison of a received contextual measure to a threshold.

In act 410, the gantry moves the source and detector to an air-calibration portion of the bore, separate from the patient-receiving portion of the bore, when air-calibration is initialized. The air-calibration portion may be distributed further along the length of the bore than the patient-receiving portion, such that when the source emits x-rays through the air-calibration portion during air-calibration, any x-ray exposure of the patient in the patient-receiving portion is reduced, though scatter radiation may still enter the patient-receiving portion. In alternative embodiments, the gantry moves the source and detector to scan the portion of the bore in which a patient is to be placed before placement of the patient.

In act 412, x-ray blocking curtains are moved to a closed position so that the curtains cover the bore. The curtains may be made from x-ray blocking material such as lead. Before the controller initiates air-calibration, the controller sends a signal to close the x-ray blocking curtains. The curtains may reduce the amount of scatter radiation that leaves the CT system during air calibration or patient scanning.

Air-calibration is initiated in act 414 by scanning air and not the patient with the x-ray source and detector. The air-scanning is performed across the bore of the CT system. In some cases, air-scanning may be performed while the patient is present in the bore. For example, the source and detector may perform air-scanning using a portion of the bore that is not occupied by the patient. In other cases, air-scanning is performed without the patient present in the bore.

Air-scanning and air-calibration may be performed in response to activation of the CT system for scanning the patient. In some cases, the air-calibration is performed using one or more of the settings for scanning a patient. For example, the air-scanning may be performed using a voltage, a focus, and/or an x-ray filter as specified in the settings for scanning the patient.

In act 416, the gain values for channels of the detector are determined. The gain is a ratio of the output signal of a channel of the x-ray detector to the intensity of an x-ray detected by the channel of the detector. The gain is set so that the same quantity of x-ray detected at each channel of the detector results in a same or similar output by each channel. For a particular voltage, focus spot, and/or x-ray filter, the detector may detect an x-ray emitted by the source. For example, the x-ray may be at a maximum intensity or exposure. In another example, the x-ray is at an intensity less than the maximum intensity or exposure. The output of the detector in response to the x-ray, combined with an offset value for the detector (e.g. the output of the detector when no x-rays are being emitted into the bore), is used to determine the gain for the channel at the particular voltage, focus spot, and/or x-ray filter.

The gain values may be determined based on the air-scanning with the settings for scanning the patient and not other settings. For example, where the settings for scanning the patient specify a particular voltage, focus spot, and x-ray filter and the air-scanning was performed using one or more of the settings for scanning the patient, the gain values may be determined for these specified scanning settings and not on other settings that were not specified for scanning the patient. In this way the gain settings may be determined for a subset of all the available voltages, focus spots, and x-ray filters. The subset matches specified settings for when the CT system is activated for scanning a patient. By determining gain settings for less than all the possible voltages, focus spots, and x-ray filters, the gain settings made be determined more quickly, thereby reducing the length of time required to perform an air-calibration. In alternative embodiments, the gain values are determined for voltages, focus spots and/or x-ray filters over the operating range. The patient-specific settings are not used to control gain determination, such as where the air calibration is triggered by change in operating environment rather than triggered by indication of intent to scan a particular patient.

In some cases, offset values for each channel of the detector are determined with and/or as part of determining the gain values. The offset values for each channel are determined when the source is not emitting x-rays into the bore. For example, the offset values are determined before the x-ray source emits x-rays to determine the gain, or after the x-ray source has finished emitting x-rays during air-calibration.

In act 418, the gantry moves the source and detector to the patient-receiving portion of the bore from the air-calibration portion of the bore. After air calibration is complete, the patient is to be scanned. The gantry positions the source and detector for scanning the patient. Alternatively, if air-calibration was performed using the bore where the patient is to be positioned (i.e., act 410 is not performed), the gantry may not need to move the source and detector again before scanning the patient.

In act 420, the patient is scanned with the x-ray source and detector. Where the air calibration was triggered in response to activation to scan a patient and receiving a setting for a medical scan, the scanning uses the setting for scanning that were also used for air calibration. Scanning occurs through the patient-receiving portion of the bore. For this situation, the patient is already in the bore. In other situations, the patient is positioned in the bore after the air calibration. Once positioned and any safety checks are performed, the technician activates the CT system, which scans the patient.

In act 422, the data acquired by the detector during scanning is used to reconstruct an image of the patient. Prior to reconstruction using computed tomography, the raw output of each channel of the detector is corrected by the gain value and/or the offset for that channel. For example, the amplitude of the output signal of a channel of the detector is increased or decreased based on the gain and/or output. Applying the gain ensures accurate output from each channel despite differences in each channel of the detector and electronic distortion in the CT system. In an alternative embodiment, the reconstruction uses the gain values determined from the air-calibration to transform the data acquired by the detector into image data.

Automatic air-calibration results in gain values that are appropriate for the settings of the x-ray source and the operating environment of the CT system. Because changing conditions can make gain values less accurate, resulting in image artifacts, the valid gain values produced by air-calibration reduce the presence of image artifacts in the reconstructed image as compared to gain values without calibration. For example, because mobile or vehicle-dispatched CT systems may encounter different scan environments for each scan, gain values for one scan may not be appropriate for the next and using the inaccurate gain values may result in image artifacts. By performing an automatic air-calibration prior to a scan, the gain values are appropriate for the scan settings and the scanning environment, resulting in fewer artifacts in the image reconstructed from the scan. Images with fewer artifacts may help determine the type of treatment for stroke patients, resulting in better treatment outcomes.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A computed tomography system, the system comprising:
   an x-ray source;
   an x-ray detector;
   a gantry configured to move the x-ray source and x-ray detector relative to an air space defined by a bore wherein the air space has a patient-receiving portion and an air-calibration portion and wherein the gantry is configured to move the x-ray source and the x-ray detector to the air-calibration portion during an air-calibration and to the patient receiving portion during scanning of the patient; and
   a controller configured to automatically initiate the air-calibration using the x-ray source and x-ray detector with air in the air space and to determine gain values for channels of the x-ray detector from the automatically initiated air-calibration and wherein the controller is also configured to automatically initiate the air-calibration upon activation of the computed tomography system for scanning a patient.

2. The system of claim 1 wherein scanning parameters for the air-calibration are the same as scanning parameters for scanning the patient.

3. The system of claim 2 wherein the scanning parameters that are the same include x-ray source voltage, x-ray source focal spot, and/or x-ray filter.

4. The system of claim 1 wherein the controller is further configured to detect the presence of the patient in the patient-receiving portion and to automatically initiate the air-calibration based on the presence of the patient in the patient-receiving portion.

5. The system of claim 1 wherein the controller is further configured to automatically initiate the air-calibration while the patient is present in the patient-receiving portion and in response to activation to start the scanning of the patient, and
   wherein the gain values from the air-calibration are used in scanning the patient.

6. The system of claim 1, wherein the controller is further configured to receive a contextual measure, compare the contextual measure to a threshold, and to automatically initiate the air-calibration when the contextual measure exceeds the threshold.

7. The system of claim 6, wherein the contextual measure is a measure of time, temperature, humidity, or location.

8. The system of claim 1, wherein the computed tomography system is a mobile computed tomography system.

9. The system of claim 1, further comprising:
   x-ray blocking curtains movable between an open and closed position,
   wherein the controller is further configured to cause the curtains to move to the closed position during the air-calibration.

10. A method of calibrating a computed tomography system having a patient bore, a controller, an x-ray source, and a detector, the method comprising:
    receiving, by the controller, a setting for a medical scan to be performed by the computed tomography system for a particular patient, the setting being one of a plurality of optional values;
    scanning air and not the patient in the patient bore with the x-ray source and the detector, the scanning using the setting;
    determining, by the controller, a gain value based on the scanning with the setting and not the other optional values;
    scanning the patient with the x-ray source and the detector using the setting and the gain value; and
    moving the x-ray source and x-ray detector by a gantry to an air-calibration portion of the patient bore during the scanning of air and to a patient-receiving portion of the patient bore during scanning of the patient.

11. The method of claim 10, wherein the setting is an x-ray source voltage, an x-ray source focal spot, and/or an x-ray filter.

12. The method of claim 10, further comprising:
    detecting the presence of the patient in the bore; and initiating, by the controller, the air scanning and automatically determining the gain value based on the determined presence of the patient.

13. The method of claim 10, further comprising:
receiving, by the controller, a contextual measure;
comparing, by the controller, the contextual measure to a threshold; and
initiating, by the controller, the air scanning and automatically determining the gain value when the contextual measure exceeds the threshold.

14. The method of claim 13 wherein the contextual measure is a measure of time, temperature, humidity, or location.

15. The method of claim 10 wherein the computed tomography system is a mobile computed tomography system.

16. The method of claim 10, further comprising:
moving x-ray blocking curtains to a closed position during air scanning.

17. The method of claim 10, wherein scanning the air and then scanning the patient are both performed in response to activation by a user of the computed tomography system for scanning the patient.

18. A method of calibrating a vehicle-dispatched mobile computed tomography system having a patient bore, an x-ray source, an x-ray detector, a gantry, and a controller, the method comprising:
moving, by the gantry, the x-ray source and the x-ray detector to an air-calibration portion of the patient bore during scanning of air and to a patient-receiving portion of the patient bore during scanning of a patient;
automatically initiating, by the controller, an air-calibration using the x-ray source and x-ray detector with air in the air-calibration portion; and
determining, by the controller, gain values for channels of the x-ray detector from the automatically initiated air-calibration.

* * * * *